Sept. 19, 1939. B. E. PRIOR Plant Pat. 340
ROSE PLANT
Filed Feb. 8, 1939
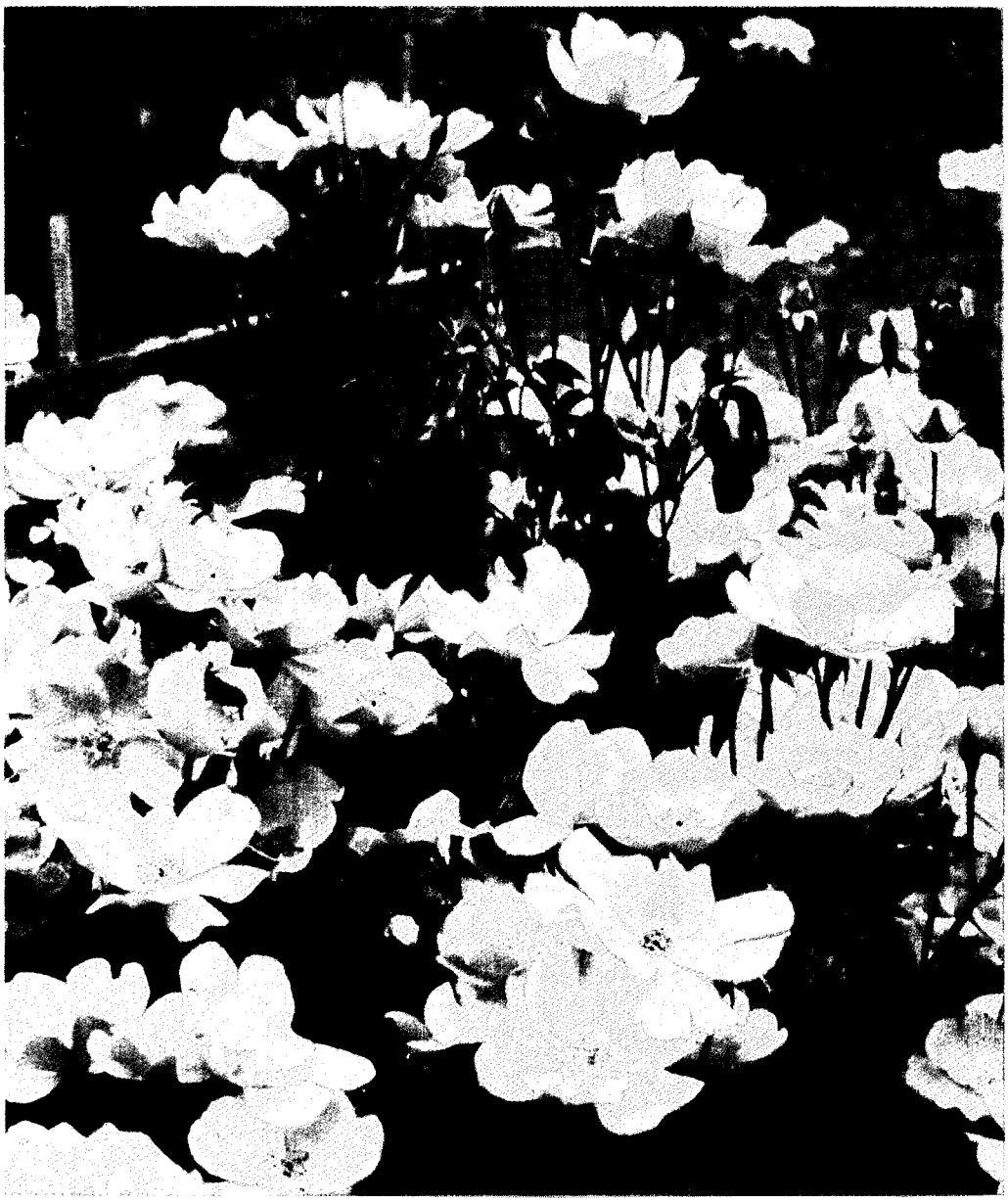
Inventor
B. E. Prior
By Robb & Robb
attorneys Patented Sept. 19, 1939

Plant Pat. 340

UNITED STATES PATENT OFFICE

340

ROSE PLANT

Basil Edmund Prior, Colchester, England, assignor to Jackson & Perkins Company, Newark, N. Y.

Application February 8, 1939, Serial No. 255,318

1 Claim. (Cl. 47—61)

The present invention relates to a new and distinct variety of rose plant in the large flowered Polyantha or Floribunda group, resulting from the crossing of Kirsten Poulsen with an unnamed seedling.

It is believed that this rose is superior to any other rose of the group aforesaid due to the size, both height and breadth, of the bush.

It is also notable that this new variety is healthier and more disease resistant than similar roses in its class, being almost immune to blackspot.

Other advantageous features reside in its greater floriferousness than any similar single or semi-double rose and in the decidedly different color of the flowers marked by very little fading and great deepening of color in the fall season.

Asexual reproduction discloses that the distinguishing characteristics come true to form.

The following is a detail description of the new variety, all references to color being in accord with Ridgway's Color Standard:—

Parentage:

*Seed parent.*—Kirsten Poulsen.

*Pollen parent.*—Unnamed seedling.

Classification:

*Botanic.*—Polyantha and large flowered Polyantha.

*Commercial.*—Floribunda.

*Flower*

(Observations made at Newark, New York in the morning of June 23, 1938.)

Blooming habit:

*Recurrent.*—Continuous.

*Other habit.*—The new flowering shoots appear immediately under the last flowers, and in rapid succession.

Bud:

*Size.*—Small.

*Form.*—Ovoid. Is not affected by wet or hot weather.

*Color.*—When sepals first divide—Plate 12, Pomegranate Purple. When petals begin to unfurl—Plate 12, Tyrian Pink. When half blown: inside of petals—Plate 1, Hermosa Pink; reverse of petals—Plate 12, Rose Color.

*Sepals.*—Smooth edge, branched. Curl back when color shows.

*Calyx.*—Shape—pear; size—long, slender; aspect—smooth. Peduncle: length—long; aspect—prickly; color—Plate 5, Cosse Green; strength—erect, slender. Opening: bud opens well; is not affected by adverse conditions.

Bloom:

*Size.*—Small.

*Average size when fully expanded.*—Three inches.

*Borne.*—In clusters, irregular.

*Stems.*—Medium length, strong.

*Form.*—When first open—cupped. Permanence—flattens.

*Petalage.*—Single (one row of petals 4 to 6). Number of petals under normal conditions—5 to 6.

*Color.*—Base of petals (aiglet)—Plate 5, Sulphur Yellow. Inside of petals—Plate 1, Shrimp Pink. Reverse of petals—Between Plate 12, Pomegranate Purple and Plate 12, Tyrian Rose.

*Variegations.*—None.

*Discoloration.*—The general tonality at the end of the first day is similar to the general impression made by *Cornus Forida rubra* flower.

Petals:

*Texture.*—Thin. Is not affected by wet or hot weather.

*Appearance.*—Inside—satiny. Outside—shiny.

*Form.*—Oval, notched.

*Arrangement.*—Regular.

*Persistence.*—Drop off cleanly.

*Fragrance.*—Slight. Other fragrance—Wild Rose fragrance.

*Lasting quality.*—On the plant and as cut flowers, very long.

Genital organs:

*Stamens, anthers.*—Small, many. Color—Plate 15, Cinnamon Brown. Arrangement—Regular around styles.

*Stamens, filaments (threads).*—Long. Color—Plate 4, Lemon Yellow.

*Pollen.*—Plate 15, Light Buff.

*Styles.*—Bunched, medium length, thin.

*Stigmas.*—White.

*Ovaries.*—All enclosed in calyx.

Fruit:

Variety is sterile with its own pollen.

*Form.*—Round.

*Aspect.*—Smooth.
*Sepals.*—Permanent; recurved, straight.

*Plant*

Form:
Bush or semi-shrub.
Growth:
Vigorous, branching.
Foliage:
5 to 7 leaflets.
*Size.*—Medium.
*Quantity.*—Abundant.
*Color.*—New foliage: upper side—Plate 4, Olive Green; mid-rib—Plate 13, Vandyke Red; under side—Plate 13, Acajou Red. Old foliage: upper side—Plate 31, Yew Green; under side—Plate 31, Light Cress Green.
*Shape.*—Oval pointed.
*Texture.*—Upper side—leathery. Under side—rough. Ribs and veins—ordinary.
*Edge.*—Serrated (saw toothed).
*Serration.*—Single, small.
*Rachis.*—Color—Plate 31, Light Cress Green. Under side—prickles.
*Stipules.*—Short, smooth.
*Disease resistance.*—Resistant, almost immune.

Wood:
*New wood.*—Color—between Plate 13, Madder Brown and Plate 31, Cress Green. Bark—smooth.
*Old wood.*—Color—Plate 31, Cress Green. Bark—smooth.
Thorns (divided into thorns, prickles and short needles):
*Thorns.*—Quantity: on main stalks from base—ordinary; on laterals from stalk—ordinary. Form—broad base, long, hooked downward. Color when young—Plate 1, Garnet Brown. Position—irregular.
*Prickles.*—Quantity: on main stalks—many; on laterals—many. Color—Plate 4, Citrine.
*Short needles.*—Quantity: on main stalks and laterals—many.

I claim:

A new and distinct variety of rose plant characterized as to novelty by the size of the bush for a Polyantha, its healthy and disease-resistant foliage, and the great floriferousness and substantially unfading color of its flowers, substantially as shown and described.

BASIL E. PRIOR.